United States Patent [19]

Billington

[11] Patent Number: 4,906,761
[45] Date of Patent: Mar. 6, 1990

[54] MYO-INOSITOL ORTHOFORMATES

[75] Inventor: David C. Billington, Hockerill, United Kingdom

[73] Assignee: Merck Sharpe & Dohme Ltd., Hoddesdon, United Kingdom

[21] Appl. No.: 212,748

[22] Filed: Jun. 28, 1988

[30] Foreign Application Priority Data

Jul. 3, 1987 [GB] United Kingdom ................. 8715635

[51] Int. Cl.$^4$ ........................................... C07D 319/08
[52] U.S. Cl. .................................... 549/358; 549/360
[58] Field of Search ............................... 549/358, 360

[56] References Cited

PUBLICATIONS

Billington & Baker, J. Chem. Soc., Chem. Commun., vol. 13, pp. 1011-1013, 1987.
deSolms et al., Tetrahedron Letters, vol. 28, No. 39, pp. 4503-4506, 1987.
Lee & Kishi, J. Org. Chem., vol. 50, p. 4402 (1985).
Ozaki et al., Tetrahedron Letters, vol. 27, pp. 3157-3160 (1986).
Vacca et al., J. Am. Chem. Soc., vol. 109, pp. 3478-3479 (1987).
Cooke & Potter, Tetrahedron Letters, vol. 28, No. 20, pp. 2305-2308 (1987).
Reese & Ward, Tetrahedron Letters, vol. 28, No. 20, pp. 2309-2312 (1987).

Primary Examiner—Nicky Chan
Attorney, Agent, or Firm—Manfred Polk; Joseph F. DiPrima

[57] ABSTRACT

This invention provides the 4-mono-anion of myo-inositol orthoformate, and describes a process for preparing this anion as well as the use of this anion in the preparation of a variety of mono- and poly-phosphate derivatives of myo-inositol.

2 Claims, No Drawings

MYO-INOSITOL ORTHOFORMATES

This invention relates to a chemical process and a novel intermediate, useful for preparing a series of myo-inosital mono- and poly-phosphates. The products of the process are important biological intermediates in the inositol secondary messenger system. Commercially these myo-inositol phosphates can be incorporated in diagnostic test kits used to assess phosphatase activity, which may be deficient or elevated in certain human disease states, such as manic depression and blood clotting disorders.

Myo-inositol is a hexa-hydroxy cyclohexane of formula I:

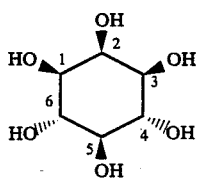

Only a relatively few phosphates of myo-inositol have been previously chemically synthesised. The only triphosphate which has been chemically synthesised is the 1,4,5-triphosphate (Vacca et al, J.A.C.S. 1987, 109, 3478; Potter et al, Tet Letters, 28, 2305; Reese et al, Tet Letters, 28, 2309; Ozaki et al, Tet Letters 27, 3157). The processes described in those publications are not readily adaptable to the preparation of other phosphates of myo-inositol. The process of the present invention enables the preparation of a variety of mono- or poly-phosphates of myo-inositol, many of which have not been previously synthesised chemically. One of the main problems in the synthesis of individual inosital phosphates is the differentiation between the hydroxyl groups to produce a selectively-protected inositol derivative.

The process of the present invention is based on a novel anion of myo-inositol orthoformate. Myo-inositol orthoformate has been described in a publication by Lee and Kishi (J. Org. Chem. 1985, 50, 4402). It has the structure II, which has the configuration shown in structure IIA.

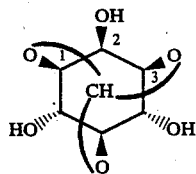

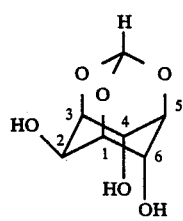

That publication describes selective protection of the equatorial hydroxyl group, i.e. the 2-hydroxyl group. Surprisingly it has now been found that formation of an anion of myo-inositol orthoformate yields a mono-anion of one of the axial hydroxyl groups in a highly selective manner. This mono-anion therefore immediately provides a distinction between the two axial hydroxyls at positions 4 and 6, and hence enables the selective synthesis of mono- or poly-phosphates of inositol.

Accordingly the present invention provides the 4-mono-anion of myo-inositol orthoformate. The anion may be associated with a metal ion and may be represented by the formula III:

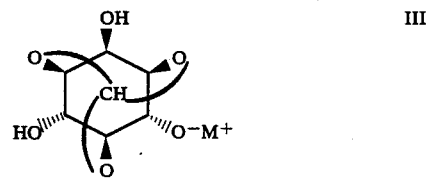

wherein $M^+$ represents a metal cation. Any metal ion may be employed, suitably an alkali metal such as lithium, sodium, and potassium. Preferably M represents sodium.

The intermediate (III) provides the basic for the synthesis of a variety of inositol phosphates. Accordingly in a further aspect, this invention provides a process for the preparation of a mono- or poly-phosphate of myo-inositol which comprises optionally protecting the 4-mono-anion of myo-inositol orthoformate with at least one removable protecting group; phosphorylating the protected intermediate; and removing any protecting groups.

Suitable protecting groups include the allyl group; $C_{1-6}$ alkyl, such as methyl; alkoxyalkyl and alkylthioalkyl such as methoxymethyl, methylthiomethyl, methoxyethoxymethyl; aryloxymethyl, such as benzyloxymethyl; aralkyl, such as benzyl, p-bromobenzyl, p-nitrobenzyl.

Any suitable phosphorylating agent may be used in the process of this invention, such as phosphonic acid or an optionally protected reactive derivative thereof. In particular the phosphorylating agent may be a compound of formula IV:

wherein $R^1$ and $R^2$ represent hydrogen or a removable protecting group, such as those specified above, and X represents a readily displaceable group. The group X may be, for example, hydroxy or halogen such as chloro or bromo.

Preferred phosphorylating agents are tetrabenzyl pyrophosphate, i.e. compound IV, $R^1=R^2=CH_2Ph$, $X=OPO(OCH_2Ph)_2$; and diphenyl chlorophosphate, i.e. compound IV, $R^1=R^2=Ph$, $X=Cl$.

The phosphorylation is carried out in any suitable solvent, in particular an aprotic solvent such as dimethylformamide.

Other suitable methods of phosphorylation include, for example, reaction of the alcohol with a phosphite, followed by oxidation and deprotection.

The ionic compound III may be employed to prepare a protected intermediate compound of formula V, which provides a further aspect of this invention:

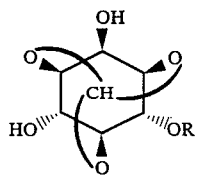

wherein R represents a readily removable hydroxy-protecting group. The group R may represent a temporary protecting group which may be removed during the reaction sequence after other hydroxyl groups have been protected using different protecting groups. By selection of a protecting group for the group R and for the other hydroxyl groups which are removable under differennt conditions, specific mono- and poly-phosphates may be prepared.

The ionic intermediate III is generally not isolated. It is conventionally prepared in an aprotic solvent, in particular dimethylformamide in the presence of a strong base, such as sodium hydride; and may be reacted in solution to introduce the desired group on the 4-hydroxyl.

The flexibility of the process of this invention may be illustrated by the following synthetic sequences to produce mono- and poly-phosphates:

(a) 1,3,4,5-tetraphosphate

When R is allyl, for example, compound V may be prepared directly from the 4-mono-anion of myo-inositol orthoformate by reaction with an allyl halide, in particular allyl bromide, $CH_2=CH.CH_2Br$. This allows protection of the 2- and 6-hydroxyl groups with less labile protecting groups such as benzyl.

Both the allyl and orthoformate groups may be removed simultaneously by isomerisation and acidic hydrolysis to leave free hdyroxyl groups at positions 1, 3, 4 and 5, which may then be phosphorylated.

(b) 4-phosphate

The 4-mono-anion of myo-inositol orthoformate may be phosphorylated directly and then deprotected. This provides a selective and efficient synthesis of myo-inositol 4-phosphate. Thus one preferred aspect of this invention provides a process for the preparation of myo-inositol 4-phosphate which comprises phosphorylating the 4-mono-anion of myo-inositol orthoformate with an optionally protected phosphorylating agent, and removing the orthoformate and any further protecting groups.

(c) 1,3-diphosphate

The orthoformate of myo-inositol may also be advantageously employed in ionic form to prepare phosphates when it is not necessary to differentiate between the axial hydroxyl groups at positions 4 and 6. For example if the 2-, 4- and 6-hydroxyl groups in compound II are protected with a protecting group which is stable to acidic hydrolysis, such as benzyl, the orthoformate group may be hydrolysed to give free hydroxyl groups at positions 1, 3 and 5. Phosphorylation leads selectively to a 1,3-diphosphate, from which the protecting groups at positions 2, 4 and 6 may be removed to give myo-inositol 1,3-diphosphate.

(d) 1-phosphate

The 1,3,5-trihydroxy, 2,4,6-protected compound, prepared as in (c) above, may be selectively phosphorylated at position 1. The protecting groups at positions 2, 4 and 6 may be removed to give myo-inositol 1-phosphate.

Other permutations of protecting groups and phosphorylation will be apparent to a man skilled in the art to prepare a desired inositol phosphate.

The following specific examples illustrate the present invention.

EXAMPLE 1 myo-inositol orthoformate myo-Inositol orthoformate was prepared by the method of Kishi et al, J. Org. Chem. 1985, 4402, and was purified by chromatography on silica gel using 80:20 dichloromethane:methanol as eluant (Rf 0.46 on silica gel TLC plate). Recrystallisation from Methanol/Chloroform gave myo inositol orthoformate (mp 300°–302° C.).

EXAMPLE 2 - Selective Benzylation

4-O-benzyl-myo-inositol orthoformate

The myo inositol-orthoformate (0.5 g, 2.6 mMol) was dissolved in dry DMF (50ml) under $N_2$, and sodium hydride was added (86 mg of an 80% dispersion, 2.8 mMol) to generate the mono anion. After stirring for 10 mins at room temperature, benzylbromide (300 μl, 440 mg, 2.6 mMol) was added and the mixture stirred at room temperature for 18 hours. 1 ml of water was added and the solvents were removed in vacuo. Chromatography on silica gel using 9:1 dichloromethane:methanol gave 4-O-benzyl-myo-inositol orthoformate 0.53 g (72%) as a thick oil. NMR δ ($CDCl_3$) 3.73 (d, J 10 Hz, 1H), 4.20 (m, 1H) 4.24 (m, 1H), 4.28 (m, 1H), 4.42 (m, 1H), 4.46 (m, 1H), 4.68 (d, 2H), 5.44 (s, 1H), and 7.39 (m, 5H).

EXAMPLE 3 - Selective Allylation

4-O-allyl-myo-inositol orthoformate

The anion of myo-inositol orthoformate formed as in Example 2 was alkylated with one equivalent of allylbromide in DMF for 18 hours. Work up and chromatography on silica gel using 60:40 ethylacetate/petroleum ether gave 4-O-allyl-myo-inositol orthoformate, as a thick oil 0.46 g (77%). NMR δ ($CDCl_3$) 3.68 (d, J10 Hz, 1H), 4.16 (m, 2H), 4.22 (m, 1H), 4.30 (m, 2H), 4.38 (m, 1H) 4.46 (m, 1H), 5.28 (m, 2H), 5.44 (s, 1H) and 5.90 (m, 1H).

EXAMPLE 4 - Selective Phosphorylation myo-inositol orthoformate-4-dibenzylphosphate The anion of myo-inositol orthoformate formed as in Example 2 was phosphorylated with one equivalent of tetrabenzyl pyrophosphate in DMF for 18 hours. Work up and chromatography on silica gel using ethylacetate gave myo-inositol orthoformate-4-dibenzylphosphate which was recrystallised from diethylether, 0.84 g (72%), mp 97°–99° C.

EXAMPLE 5

Synthesis of myo-inositol-1,3,4,5-tetraphosphate (a) 2,6-di-O-benzyl(-4-O-allyl)-myo-inositol orthoformate 4-O-Allyl-myo-inositol orthoformate (4.8 g, 20.7 mMol) was dissolved in dry DMF (250 ml) and treated with NaH (2.3 g of an 80% dispersion 83 mMol). After stirring for 20 mins at room temperature, benzyl bromide (14.2 g, 83 mMol) was added and the mixture stirred at room temperature for 18 hours. Water (10 ml) was added and the solvents removed in vacuo. The residue was partitioned between $CHCl_3$ and water and the $CHCl_3$ layer washed with water, dried and evaporated. Chromatography on silica gel using 3:7 ethylacetate:petroleum ether gave 2,6 di-O-benzyl(-4-O-allyl)-myo-inositol orthoformate as a thick oil. 7.1 g (86%) NMF δ ($CDCl_3$), 4.00 (m, 2H), 4.28 (m, 4H), 4.40 (m, 1H), 4.54 (q, 2H), 4.7 (S, 2H), 5.20 (m, 2H), 5.54 (s, 1H), 5.84 (m, 1H), and 7.3 (m, 10H).

(b) 2,6di-O-benzyl-myo-inositol 2,6-Di-O-benzyl(-4-O-allyl)-myo-inositol (7.1 g, 17 mMol) was dissolved in 550 ml of 10% aqueous ethanol, and to the solution Wilkinson's catalyst (0.5 g) and DABCO (0.2 g) were added. The solution was boiled under reflux under nitrogen for 9 hours. The solution was filtered and the solvents removed in vacuo. The residue was taken up in methanol (700 ml) and 10N HCl was added (7 ml). The mixture was boiled under reflux for 20 min, cooled, and adjusted to pH 8 with 880 ammonia solution. The solvents were removed in vacuo an the residue extracted with boiling ehtyl acetate (total 11). The solvent was removed in vacuo and the residue recrystallised from $CHCl_3$/petroleum ether to give 2,6-di-O-benzyl-myo-inositol, 3.3 g (53%) mp 119°–120.5° C.

(c) 2,6-di-O-benzyl-myo-inositol-1,3,4,5, tetrakisdibenzylphosphate

Sodium hydride (240 mg of an 80% dispersion, 8 mMol) was washed free of oil and suspended in anhydrous THF (70 ml) under $N_2$. 2,6-di-O-benzyl-myo-inositol (360 mg, 1 mMol) was added and the solution heated to 60° C. for 15 min. After cooling to room temperature, tetrabenzylpyrophosphate (3.26 g, 6 mMol) was added followed by imidazole (50 mg) and the solution was stirred at room temperature for 18 hours. The solution was filtered and the filter cake washed with THF (2×25 ml). The solvent was removed in vacuo and the residue chromatographed on silica gel using 6:4 ethylacetate:petroleum ether to give 2,6-di-O-benzyl-myo-inositol-1,3,4,5 tetrakisdibenzylphosphate, 920 mg (66%) as a thick oil. NMR δ ($CDCl_3$) 4.06 (t, 1H), 4.22 (m, 1H), 4.30 (m, 1H), 4.44 (q, 1H), 4.60–5.10 (complex m, 22H) and 7.20 (m, 50H).

(d) myo-inositol-1,3,4,5-tetraphosphate 2,6-Di-O-benzyl-myo-inositol-1,3,4,5 tetrakisdibenzylphosphate (0.15 g, 0.1 mMol) was dissolved in 20% aqueous ethanol (100 ml) and hydrogenated over 100 mg of 10% Pd on carbon at 50 psi for 10 hours. The solution was filtered and the solvents removed in vacuo. The residue was taken up in water (10 ml) and passed down a column of Dowex 50×8.200 in the acid form. Excess cyclohexylamine was added to the eluate and after 1 hour the aqueous solution was extracted with diethyl ether. The aqueous layer was freeze dried and the residue recrystallised from water and acetone to give myo-inositol-1,3,4,5 tetraphosphate as its hexacyclohexylammonium salt, 115 mg (88%) m.p. 175°–177° C. ($H_2O$/acetone), NMR ($^2H_2O$) δ 3.84 (t, J 10 Hz, 1H, $H_6$), 3.93 (td, J 10 and 3 Hz, 1H, $H_1$), 3.95 (m, 1H, $H_5$), 4.02 (td, J 10 and 3 Hz, 1H, $H_3$), 4.31 (q, J 10 Hz, 1H, $H_4$) and 4.32 (bs, 1H, $H_2$) m/s FAB+ 600 (M+cyclohexylamine+H), FAB− 499 (M-H)−.

EXAMPLE 6

Synthesis of myo-inositol-4-phosphate myo-Inositol-4-dibenzylphosphate (440 mg, 0.97 mMol) was dissolved in 20% aqueous ethanol (240 ml) and hydrogenated over 10% Pd on carbon (250 mg) at 50 psi for 18 hours. The solution was filtered and the solvents removed in vacuo. The residue was dissolved in 20% aqueous TFA (50 ml) and stirred at room temperature for 4 hours. The solvent was removed in vacuo and the residue in water (10 ml) passed down a column of Dowex 50×8.200 in the acid form. The eluate was treated with excess cyclohexylamine and after 1 hour the aqueous solution was extracted with diethyl ether and freeze dried. The residue was recrystallised from water and acetone to give myo-inositol-4-phosphate as its biscyclohexylammonium salt mp. 133°–134° C. ($H_2O$/acetone) NMR δ ($^2H_2O$) 3.41 (t, J 9 Hz, 1H, $H_5$ or $H_6$), 3.55 (dd, J 9 and 2.5 Hz, 1H, $H_1$ or $H_3$), 3.63 (dd J 9 and 2.5 Hz, 1H, $H_1$ or $H_3$), 3.70 (t, J 9 Hz, 1H, $H_5$ or $H_6$), 4.05 (m, 1H, $H_2$) and 4.11 (t, J 9 Hz, 1H, $H_4$); m/s FAB+ 360 (M+cyclohexylamine)+ FAB− 259 (M-H)−, in quantitative yield.

EXAMPLE 7

Synthesis of myo-inositol-1,3,-bisphosphate (a) 2,4,6-tri-O-benzyl-myo-inositol orthoformate myo-Inositol orthoformate (5 g, 26 mMol) was dissolved in dry DMF (250 ml) and sodium hydride (4 g of an 80% dispersion, 133 mMol) was added. The mixture was stirred under $N_2$ for 20 min and then benzyl bromide (21.6 g, 130 mMol) was added over 20 min with cooling. After stirring at room tempeature for 18 hours, water (10 ml) was added slowly and the solvents removed in vacuo. The residue was partitioned between $CHCl_3$ and water and evaporation of the organic layer gave the crude product, 17 g, which was recrystallised from petroleum ether to give 2,4,6-tri-O-benzyl-myo-inositol orthoformate, 9.5 g (79%) mp 102°–104° C.

(b) 2,4,6-tri-O-benzyl-myo-inositol 2,4,6-Tri-O-benzyl-myo-inositol orthoformate (6 g, 13 mMol) was dissolved in methanol (500 ml) and concentrated HCl (5 ml) was added. The solution was boiled under reflux for 25 min, cooled to room temperature and adjusted to pH 8 with 880 ammonia solution. The solvents were removed in vacuo and the residue extracted with ethyl acetate (2×250 ml). The solvent was removed in vacuo and the residue recrystallised from diethylether/petroleum ether, to give 2,4,6-tri-O-benzyl-myo-inositol, 5.1 g (87%) mp 83°–84.5° C.

(c) 2,4,6-tri-O-benzyl-myo-inositol-1,3-bis (diphenyl)phosphate 2,4,6-Tri-O-benzyl-myo-inositol (4 g, 8.8 mMol) was dissolved in dry $CH_2Cl_2$ (300 ml) and treated with DMAP (300 mg) triethylamine (12 ml) and finally diphenylchlorophosphate (4.0 ml 19.3 mMol). The solution was stirred at room temperature for 5 hours. The solvent was removed in vacuo and the residue partitioned between water and diethyl ether. The organic phase was washed with water and brine, dried and evaporated in vacuo. The residue was chromatographed on silica gel using 4:6 ethylacetate: petroleum ether to give a mixture of 1,3 and 1,5 diphosphorylated products. 2,4,6-tri-O-benzyl-myo-inositol 1,3-bis(dephenyl)phosphate was obtained from the mixture by selective crystallisation from diethylether/petroleum ether, 3.1 g (38%) mp. 109°-110° C.

(d) myo-inositol-1,3,bisphosphate tetracyclohexylammonium salt

A solution of 2,4,6-tri-O-benzyl-myo-inositol-1,3, bis(dephenyl)phosphate (500 mg, 0.54 mMol) in 10 ml of dry THF was added dropwise to a solution of lithium metal (ca 20 mg) in 2:1 liquid ammonia: THF (75 ml) at −78° C. under nitrogen until the blue colour was discharged. A ca 10 mg pellet of lithium was then added and the blue colour titrated to colourless with more substrate solution. This process was repeated until all of the substrate solution had been added (total time 1 hr). A further 20 mg of lithium was added and the blue solution stirred at −78° C. for 15 min. Water (2 ml) was added and the solvents allowed to evaporate overnight. The residue was dissolved in water (20 ml) and passed through a column of amberlite IR 120 in the H+ form using water as eluant. The acidic fractions were combined, treated with excess cyclohexylamine, and stirred for 1 hour. The solution was extracted with diethyl ether and freeze dried to give myo-inositol-1,30bisphosphate tetracyclohexylammonium salt, which was recrystallised from water and acetone, 270 mg (66%) mp. 165°-166° C. (H$_2$O/acetone) NMR δ ($^2$H$_2$O) 3.40 (t, J 9 Hz, 1H, H$_5$), 3.78 (t, J 9 Hz, 2H, H$_4$+H$_6$), 3.96 (dt, J 9 and 3 Hz, 2H, H$_1$+H$_3$) and 4.28 (t, J 3 Hz, 1H, H$_2$); m/s FAB+ 440 (M+cyclohexylamine+H)+, FAB− 339 (M-H)−.

EXAMPLE 8

Synthesis of myo-inositol-1-phosphate (a) 2,4,6-tri-O-benzyl-myo-inositol-1-dibenzylphosphate 2,4,6-Tri-O-benzyl-myo-inositol (500 mg, 1.1 mMol) was dissolved in dry DMF (50 ml) and sodium hydride (73 mg of an 80% dispersion, 2.2 eq) was added. The suspension was stirred for 10 min under N$_2$ and tetrabenzylpyrophosphate (1.2 g, 2.2 mMol) was added. The mixture was stirred at room temperature for 18 hours, quenched with 1 ml sat NH$_4$Cl solution, and the solvents removed in vacuo. The residue was taken up in CH$_2$Cl$_2$, filtered, and the filtrate evaporated in vacuo. The residue was chromatographed on silica gel using diethyl ether to give 2,4,6-tri-O-benzyl-myo-inositol-1-dibenzylphosphate as a thick oil, 300 mg (42%) NMR δ (CDCl$_3$) 3.50 (m, 2H), 3.64 (t, 1H), 3.88 (t, 1H), 4.18 (t, 1H), 4.28 (m, 1H), 4.70-5.00 (m, 10H) and 7.30 (m, 25H).

(b) myo-inositol-1-phosphate biscyclohexylammonium salt 2,4,6-di-O-benzyl-myo-inositol-1-dibenzylphosphate is converted into myo-inositol-1-phosphate biscyclohexylammonium salt following the procedure of Example 5.

What is claimed is:

1. A compound of formula III

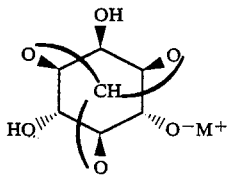

wherein M+ represents a metal cation.

2. Compound as claimed in claim 1 wherein M represents sodium.

* * * * *